US009386941B2

(12) United States Patent
Piferi et al.

(10) Patent No.: US 9,386,941 B2
(45) Date of Patent: Jul. 12, 2016

(54) TABLE STABILIZERS FOR SCANNER SYSTEMS

(71) Applicant: MRI Interventions, Inc., Memphis, TN (US)

(72) Inventors: Peter Piferi, Orange, CA (US); Kamal Vij, Chandler, AZ (US); Scott Arnold, Fullerton, CA (US)

(73) Assignee: MRI International, Inc., Irvine, CA (US)

( * ) Notice: Subject to any disclaimer, the term of this patent is extended or adjusted under 35 U.S.C. 154(b) by 148 days.

(21) Appl. No.: 14/290,051

(22) Filed: May 29, 2014

(65) Prior Publication Data

US 2015/0011869 A1    Jan. 8, 2015

Related U.S. Application Data

(60) Provisional application No. 61/841,987, filed on Jul. 2, 2013.

(51) Int. Cl.
*A61B 5/055* (2006.01)
*A61B 6/04* (2006.01)

(52) U.S. Cl.
CPC ............. *A61B 5/0555* (2013.01); *A61B 6/0407* (2013.01)

(58) Field of Classification Search
CPC ............................ A61B 5/0555; A61B 6/0407
See application file for complete search history.

(56) References Cited

U.S. PATENT DOCUMENTS

| 5,735,278 | A  | 4/1998  | Hoult et al.    |
| 6,396,271 | B1 | 5/2002  | Burl et al.     |
| 8,099,150 | B2 | 1/2012  | Piferi et al.   |
| 8,190,235 | B2 | 5/2012  | Scarth et al.   |
| 8,548,569 | B2 | 10/2013 | Piferi et al.   |

OTHER PUBLICATIONS

Visius® Surgical Theater Brochre, IMRIS, http://www.imris.com/content/visius-surgical-theatre-brochure. 7 pages, date unknown but believed to be prior to the priority date of the present application, printed from the Internet May 9, 2014.

*Primary Examiner* — Mark Remaly
(74) *Attorney, Agent, or Firm* — Myers Bigel & Sibley, P.A.

(57) ABSTRACT

Scanner Systems with table stabilizers for stabilizing patient support structures during a surgery include a stabilizer block that can cooperate with the gantry to structurally support a head end portion of the table to prevent undesired movement of the table under an end load.

24 Claims, 11 Drawing Sheets

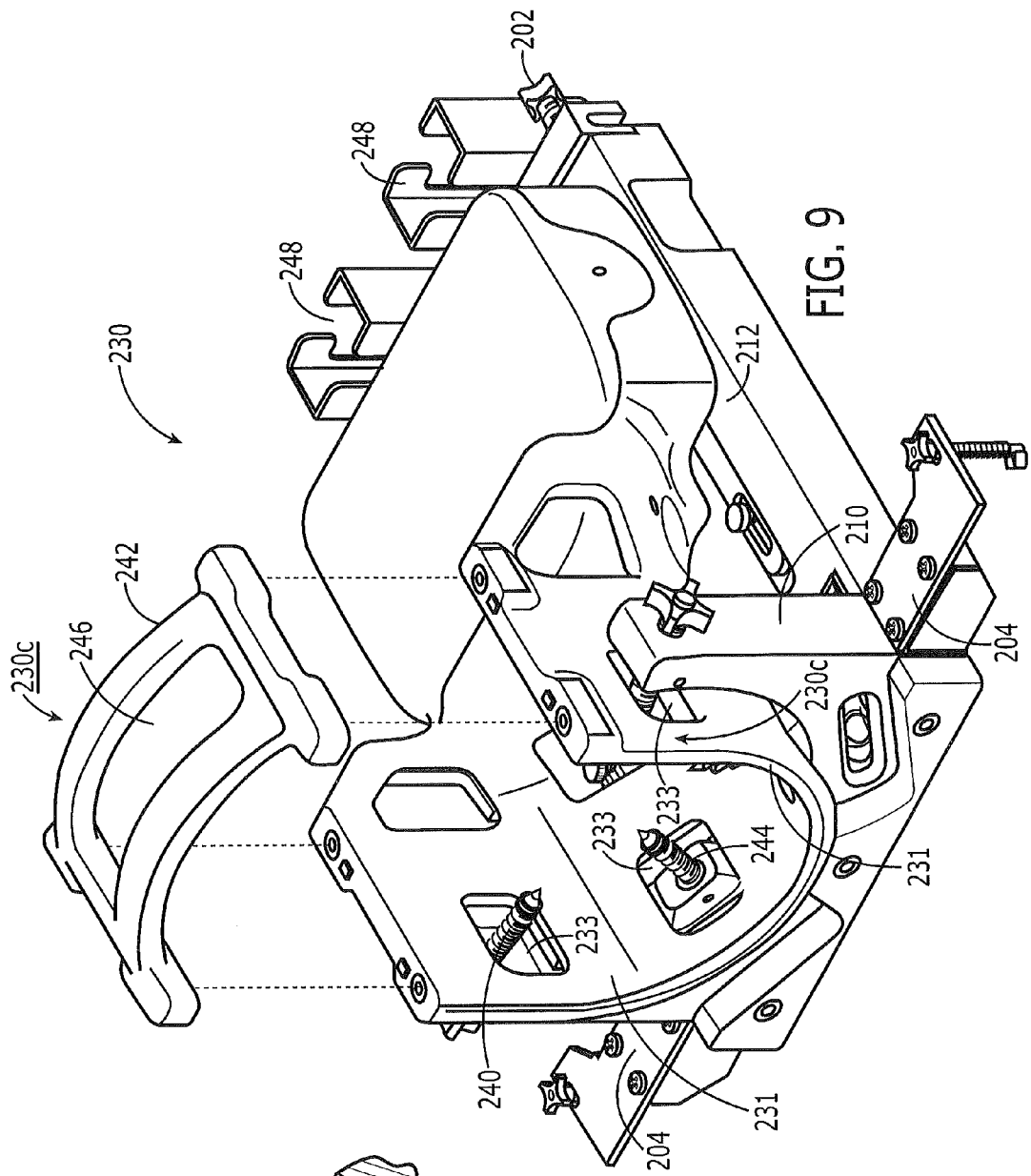
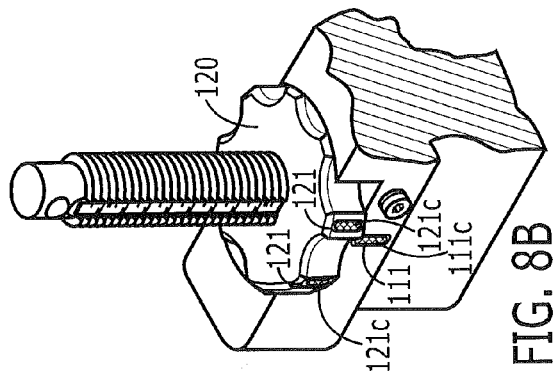
FIG. 9
FIG. 8B

TABLE STABILIZERS FOR SCANNER SYSTEMS

RELATED APPLICATIONS

This application claims priority to and the benefit of U.S. provisional patent application Ser. No. 61/841,987, filed Jul. 2, 2013, the contents of which are hereby incorporated by reference as if recited in full herein.

FIELD OF THE INVENTION

The present invention relates generally to medical systems and apparatus and, more particularly, to CT and/or MRI-interventional systems and apparatus.

BACKGROUND

Intra-operative Scanner systems, such as MRI Scanner systems, include the MRI Scanner with a high-field magnet with a magnet bore and a gantry that typically moves in a longitudinal direction in and out of the bore of the magnet. During MRI-Guided surgeries, it can be desired to drill through bone, such as a skull, to provide access for and/or define a surgical path for passing medical interventional devices.

SUMMARY

Embodiments of the invention are directed to table stabilizers that can attach to a gantry and/or table to prevent an end of the table from bending, flexing and/or moving downward under a load on an end of the table.

According to some embodiments of the present invention, the table stabilizer can cooperate with a head coil and/or an apparatus for securing various types of head support frames within a bore of an MRI scanner. The table stabilizer can be formed entirely of MRI compatible material and can engage sidewalls of a gantry associated with an MRI scanner.

Some aspects of the invention are directed to table stabilizers for a CT and/or MRI Scanner system. The table stabilizers include: a stabilizer block for a table that cooperates with a CT and/or MRI Scanner; at least one upwardly extending rod attached to the stabilizer block; and an upper stabilizer support attached to the at least one upwardly extending rod to thereby allow the upper stabilizer support to be vertically adjusted relative to the stabilizer block.

The table stabilizer can include a capture block that is attachable to a head fixation assembly. The upper stabilizer support can include first and second laterally spaced apart risers residing on opposing sides of an open medial segment. The capture block can be configured to be received in the open medial segment to rest on the upper stabilizer support.

The table stabilizer block can include at least one drive wheel attached to a respective at least one upwardly extending rod to allow a user to turn the drive wheel to vertically adjust the height of the upper stabilizer support relative to the stabilizer block.

The at least one upwardly extending rod can include first and second laterally spaced apart upwardly extending threaded rods. The at least one stabilizer block can include first and second laterally spaced apart drive wheels, the first drive wheel attached to the first upwardly extending threaded rod and the second drive wheel attached to the second upwardly extending threaded rod.

The stabilizer block can include a lower lateral adjustment slider configured as a base with laterally extending slots that holds the stabilizer block and allows a user to laterally adjust the position of the stabilizer block in the base.

The at least one upwardly extending rod can include visual indicia of height and/or position.

The threaded rods each can include a scale for visual indicia of height and/or position.

The first and second drive wheels can include circumferentially spaced apart visual indicia for identifying a rotational position. The stabilizer block can include first and second receptacles in an upper surface of the stabilizer block, the first receptacle holding the first drive member and the second receptacle holding the second drive member, each receptacle can be configured so that an outer perimeter of a respective drive wheel extends outside a corresponding receptacle to allow a user to rotate the drive wheel while held in the corresponding receptacle. The stabilizer block includes visual indicia of alignment, positioned adjacently below each of the first and second receptacles.

The stabilizer block includes a pair of outwardly extending upper arms on opposing lateral sides thereof that slidably rest on support surfaces of a bore of the CT and/or MRI gantry. The stabilizer block can include at least one receptacle in an upper surface of the stabilizer block that holds a respective one of the at least one drive member.

The capture block can include laterally extending arrows to thereby provide visual alignment indicia for placement in the medial open segment between the risers.

All components of the table stabilizer can be fabricated from MRI compatible material.

Other embodiments are directed to an MRI or CT Scanner system. The system includes: a CT or MRI Scanner having a gantry and a bore extending through the gantry; a patient table configured to be received in the bore of the gantry; and a table stabilizer that resides under and is attached to one end portion of the table and that is supported by a floor also supporting the patient table.

The table stabilizer can include: a stabilizer block configured to engage support surfaces of an inner wall of the bore of the gantry; at least one upwardly extending rod attached to the stabilizer block; and an upper stabilizer support attached to the at least one upwardly extending rod to thereby allow the upper stabilizer support to be vertically adjusted relative to the stabilizer block.

The table stabilizer can also include a capture block that is attachable to a head fixation assembly and/or a table extension. The upper stabilizer support comprises first and second laterally spaced apart risers residing on opposing sides of an open medial segment. The capture block can be configured to be snugly received in the open medial segment to rest on the upper stabilizer support.

The stabilizer block includes at least one drive wheel attached to a respective at least one upwardly extending rod to allow a user to turn the drive wheel to vertically adjust the height of the upper stabilizer support relative to the stabilizer block.

The at least one upwardly extending rod can include first and second laterally spaced apart upwardly extending threaded rods and the at least one drive wheel can include first and second laterally spaced apart drive wheels, the first drive wheel attached to the first upwardly extending threaded rod and the second drive wheel attached to the second upwardly extending threaded rod.

The stabilizer block can include a lower lateral adjustment slider configured as a base with laterally extending slots that holds the stabilizer block and allows a user to laterally adjust the position of the stabilizer block in the base.

The at least one upwardly extending rod can include visual indicia of height or position.

The threaded rods can each comprise a scale for visual indicia of height and/or position. The drive wheels can include circumferentially spaced apart visual indicia for identifying a rotational position. The stabilizer block can include first and second receptacles in an upper surface of the stabilizer block, the first receptacle holding the first drive member and the second receptacle holding the second drive member, each receptacle configured so that an outer perimeter of a respective drive wheel extends outside a corresponding receptacle to allow a user to rotate the drive wheel while held in the corresponding receptacle. The stabilizer block can include visual indicia of alignment, positioned adjacently below each of the first and second receptacles.

The stabilizer block can include a pair of outwardly extending upper arms on opposing lateral sides thereof that slidably rest on support surfaces of an inner wall of the gantry bore. The stabilizer block can include at least one receptacle in an upper surface of the stabilizer block that holds a respective one of the at least one drive member.

The capture block can include laterally extending arrows to thereby provide visual alignment indicia for placement in the medial open segment between the risers.

The system can include an MRI system with a movable magnet having the gantry with the bore, wherein the patient table comprises a pedestal that is stationary and affixed to a floor. The table stabilizer engages an inner wall of the bore of the magnet, and wherein all the table stabilizer components are fabricated from MRI compatible material.

Other embodiments are directed to MRI Scanners that include: a longitudinally moving gantry with a magnet having a bore with an inner wall; a patient table supported by a pedestal to be in a fixed position on a floor; a table stabilizer residing under and attached to (i) a table extension and/or an MRI compatible head support frame and (ii) a lower portion of the inner wall of the gantry bore, and wherein the table stabilizer is configured to have lateral and vertical adjustability relative to the patient table and/or position in the magnet bore.

Still other embodiments are directed to methods of supporting a head coil in a bore of a magnet of an MRI Scanner during an MRI-guided procedure. The methods include: providing a head fixation assembly with a head coil; providing a patient table with a table stabilizer attached thereto so as to reside under a table extension and/or head end portion of the patient table; placing a patient on the patient table with a head of the patient in the head fixation assembly; moving either (a) the patient table with the table stabilizer or (b) moving the magnet so that the patient on the patient table resides in the magnet bore and the table stabilizer engages an inner wall of the bore of the magnet; and performing an MRI-guided procedure with the patient on the patient table in the magnet bore thereby providing additional structural rigidity/support to inhibit downward movement of the head fixation assembly due to pressure applied to the head of a patient held in the head fixation assembly during an MRI guided procedure.

The moving step can be carried out by moving the magnet while the patient table is in a fixed position using a pedestal support.

The table stabilizer can reside under and have a component that attaches to an MRI compatible head support frame for adjustably immobilizing the head of a patient during a medical procedure, and optionally to allow the head support frame to be moved to any of a plurality of locations across the width of the gantry.

The head support frame includes a pair of head engagement arms that extend outwardly in adjacent, spaced-apart relationship. Each head engagement arm has a free end and at least one head fixation member configured to engage a patient's head within the head support frame and restrain the patient's head from movement. In addition, the head support frame is rotatable about two orthogonal axes so as to be positioned at any of a plurality of angles relative to the gantry.

The table stabilizer can cooperate with a head coil assembly and/or head fixation assemblies and may be particularly suitable for placing neuro-modulation leads, such as Deep Brain Stimulation ("DBS") leads, implantable parasympathetic or sympathetic nerve chain leads and/or CNS stimulation leads, as well as other devices within the brain. Embodiments of the present invention may be suitable for a number of MRI-guided drug delivery procedures, particularly precision delivery procedures and/or MRI-guided ablation procedures, etc.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 9 is a side perspective view of an exemplary head coil with head fixation members according to embodiments of the present invention.

DETAILED DESCRIPTION

Figure 1A:
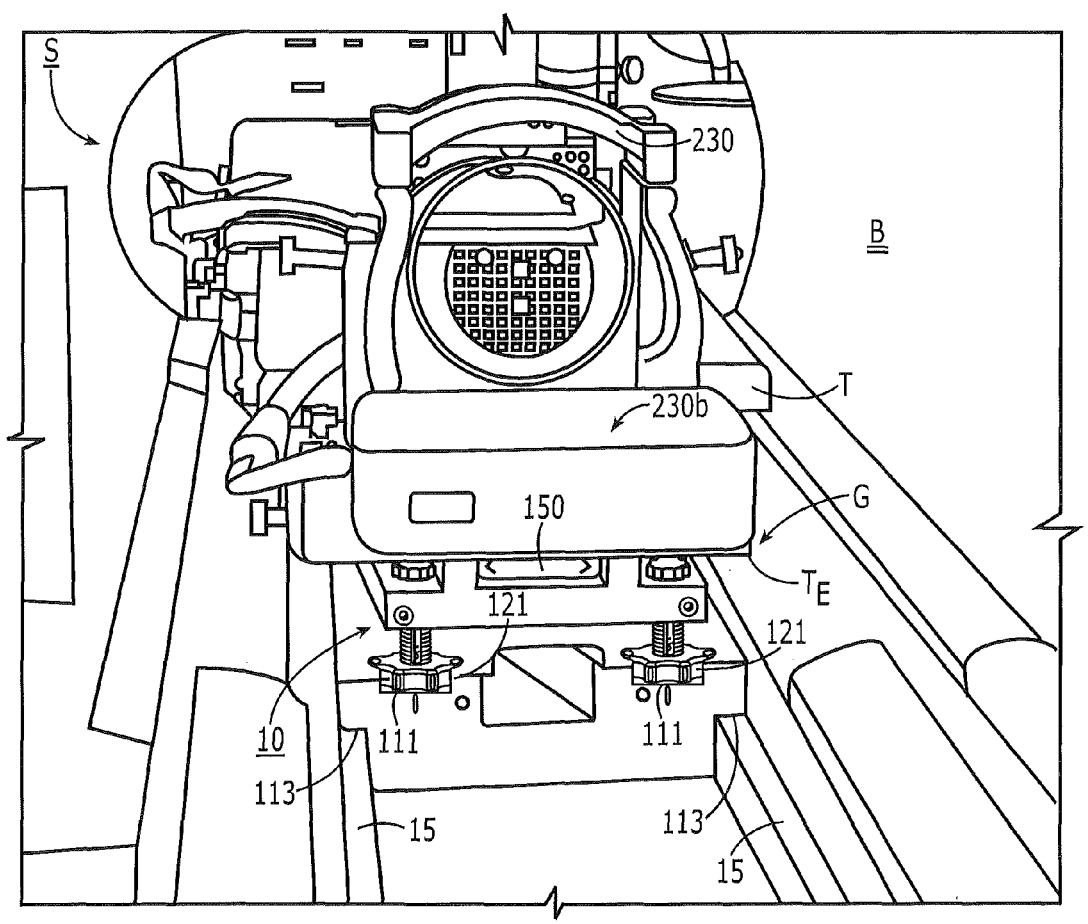
FIG. 1A is an end perspective view of an MR Scanner system with a table, table stabilizer and head coil in a gantry according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/−twenty percent (20%).

The term "rod" refers to an elongate member with rigidity, such as a bolt, pin, screw, etc.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "gantry" refers to a device holding imaging components about a patient portal. The gantry can be relatively short for CT Scanners and may be part of a cylindrical patient space for MRI Scanners.

The term "head fixation member" refers to an elongate member with sufficient structural rigidity to secure and/or move the head of a patient and may take the form of a bolt, pin, screw, etc. Head fixation members according to various embodiments of the present invention may be threaded skull pins.

The term "head fixation assembly" refers to an assembly including at least a head support frame and a base for supporting the head support frame. Head fixation assemblies according to various embodiments of the present invention may further include or cooperate with an RF head coil apparatus and/or associated components, as further described in more detail below.

Head fixation assemblies according to embodiments of the present invention can facilitate guiding and/or placing diagnostic or interventional devices and/or therapies to any desired internal region of the brain. For example, head fixation assemblies according to embodiments of the present invention facilitate the placement of implantable DBS leads for brain stimulation, typically deep brain stimulation, and facilitate delivering tools or therapies that stimulate a desired region of the sympathetic nerve chain and/or that deliver drug therapies. Embodiments of the present invention can be used with any MRI scanner system, including open and closed bore designs and any field strength, typically 1.0 T (Tesla)-10 T, such as about 1.5 T, 2 T and 3 T.

Embodiments of the present invention have other uses inside or outside the brain including stem cell placement, gene therapy or drug delivery for treating physiological or other conditions. Some embodiments can be used to treat tumors. Some embodiments can be used for diagnosing or delivering any desired therapy such as, for example, RF stimulation or ablation, laser stimulation or ablation, cryogenic stimulation or ablation, etc.

As shown in FIG. 1A, embodiments of the invention provide table stabilizers 10 to cooperate with patient support tables T for medical imaging platforms with Scanners S, such as intra-operative systems. The table stabilizer 10 may also be configured only for CT Scanner systems, only MRI systems, or be configured for both MRI and CT Scanner systems and/or combined imaging systems.

Figure 1B:
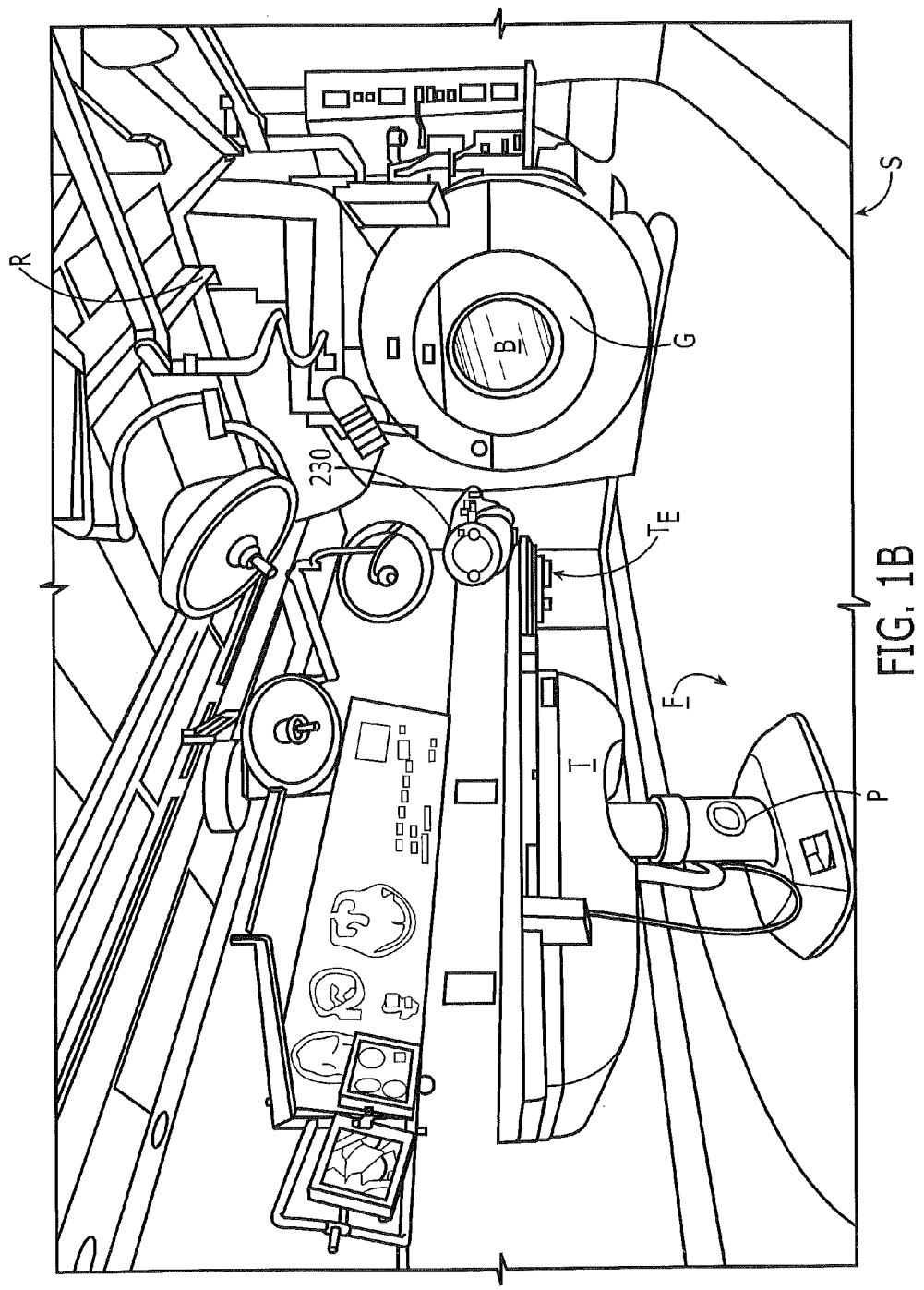
FIG. 1B is a side perspective view of an exemplary patient support table for the table stabilizer in a moveable magnet/gantry system according to embodiments of the present invention.

As shown in FIG. 1B, in some embodiments, the table stabilizer 10 is configured to cooperate with the surgical table T having a fixed or stationary position with a movable, ceiling mounted rails R allowing a movable MR and/or CT scanner S.

In some embodiments, the table T is configured to cooperate with an MR Scanner S that is part of a VISIUS® surgical theatre from IMRIS, Inc. (Minneapolis, Minn.), which is a multifunctional surgical environment with a high-field MR and/or multi-slice CT scanner that can travel on ceiling mounted rails while the patient table, typically a pedestal mounted table, remains in a fixed position. See, e.g., U.S. Pat. Nos. 8,190,235 and 5,735,278, the contents of which are hereby incorporated by reference as if recited in full herein.

As shown in FIG. 1A, the table stabilizer 10 can engage support surfaces 15 formed through a gantry G of a Scanner system S. As is well known, the gantry G can provide a patient portal or bore B and can be relatively short for CT Scanners and may be part of a longer cylindrical patient space associated with a magnet for an MRI Scanner S. The table stabilizer 10 can reside under the end of the table T, typically a front end (or extension) of the table $T_E$ under at least a portion of an RF head coil 230, typically under a flat end portion of the head coil 230b.

The table stabilizer 10 can be directly or indirectly supported by a floor F of the operating suite or room. The table stabilizer 10 is configured to engage an underside of the table T to provide structural support for the front end of the table $T_E$ to prevent any vertical movement during a surgical procedure where precision is needed for image-guided surgery, typically neurological (brain) surgeries, but may be of use in other surgeries as well. For pedestal style tables T (FIG. 1A), for example, the table stabilizer 10 can be configured to mount to the floor and the underside of the table T to push up against the underside of the table T while the pedestal P holds the table in place and pushes down (anchored to floor) against the table stabilizer 10 to lock the end of the table $T_E$ in position.

In some embodiments, as shown in FIG. 1A and FIGS. 10A-10C, the table stabilizer 10 can be configured to rest against support surfaces 15 of the inner lower wall W of the scanner bore B, typically under the table T.

FIGS. 2A, 3, 7 and 8A illustrate an example of the table stabilizer 10. As shown, the table stabilizer 10 includes a stabilizer block 110 that holds an upper stabilizer support 140. The table stabilizer 10 can include at least one upwardly extending rod 130 that allows for vertical height adjustment of the upper stabilizer support 140 relative to the stabilizer block 110. The table stabilizer 10 can include at least one (shown as a pair of) drive wheel 120 (which can be configured as "knobs"). The drive wheel 120 can threadably attach to a respective upwardly extending rod 130 that allows for vertical adjustment of the upper stabilizer support 140. The rod 130 may be threaded as shown or may have another structural configuration that allows for the vertical adjustment of the upper support 140. The vertical adjustment can be configured to be provided with other user inputs such that the drive wheel(s) 120 is not required.

The stabilizer block 110 can include outer arms 113 that engage support surfaces 15. The stabilizer 10 can be stationary with the table T (FIG. 1B).

In other embodiments, the gantry G can be stationary and the table T and stabilizer 10 can engage rails to slidably move back and forth on the rails. That is, the support surfaces 15 can be configured as rails in longitudinally stationary gantry systems that allow the table T and/or stabilizer block 110 to slidably translate back and forth. Other gantry engagement configurations may use other stabilizer block engagement configurations. Thus, embodiments of the invention can have other gantry-engagement configurations or may mount to the floor directly or indirectly.

Referring again to FIGS. 2A, 3, 7 and 8A, the rods 130 can include visual height indicia 136 in a suitable scale, typically English and/or metric and providing a range of between about 0-3 inches (0-76 mm) and/or between about 0-9 cm or more, e.g., between about 0-6 inches and/or 0-18 cm or more, so that the stabilizer support 140 can reside at various different heights above the stabilizer block 110.

As shown, the indicia 136 can include an upright scale or ruler 136 that can be attached to an upwardly extending flat surface 130f in the threaded rod 130. The scale or ruler 136 can be attached with adhesive or double-sided adhesive tape or other suitable fixation technique. Optionally, the scale or ruler can be printed, sublimated or otherwise applied directly onto a surface of the threaded rod 130.

Figures 2A, 2B:
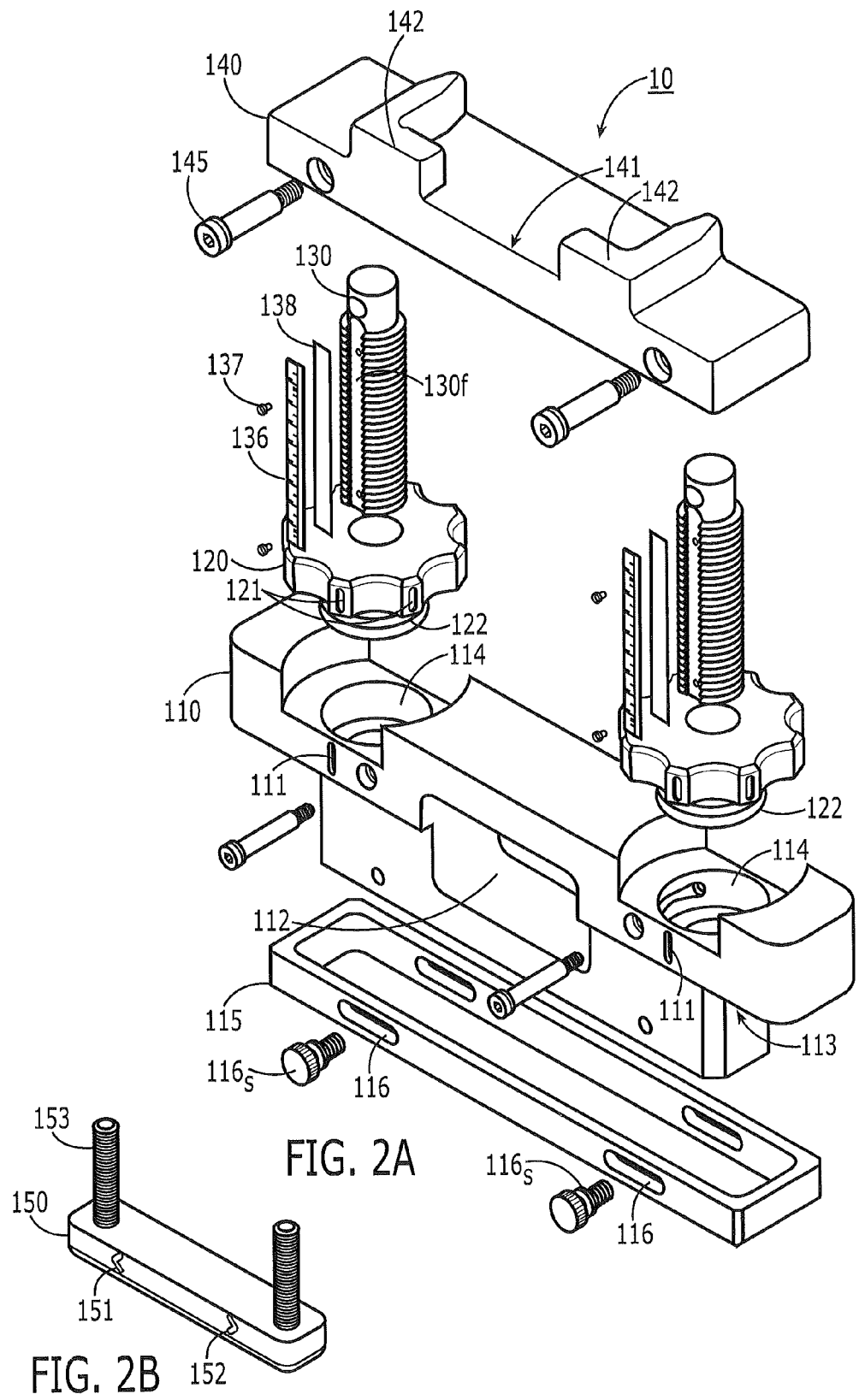
FIG. 2A is a front perspective exploded view of a table stabilizer assembly according to some embodiments of the present invention.
FIG. 2B is a front perspective view of a capture block that can attach to a head coil and cooperate with the table stabilizer shown in FIG. 2A according to embodiments of the present invention.
Figure 3:
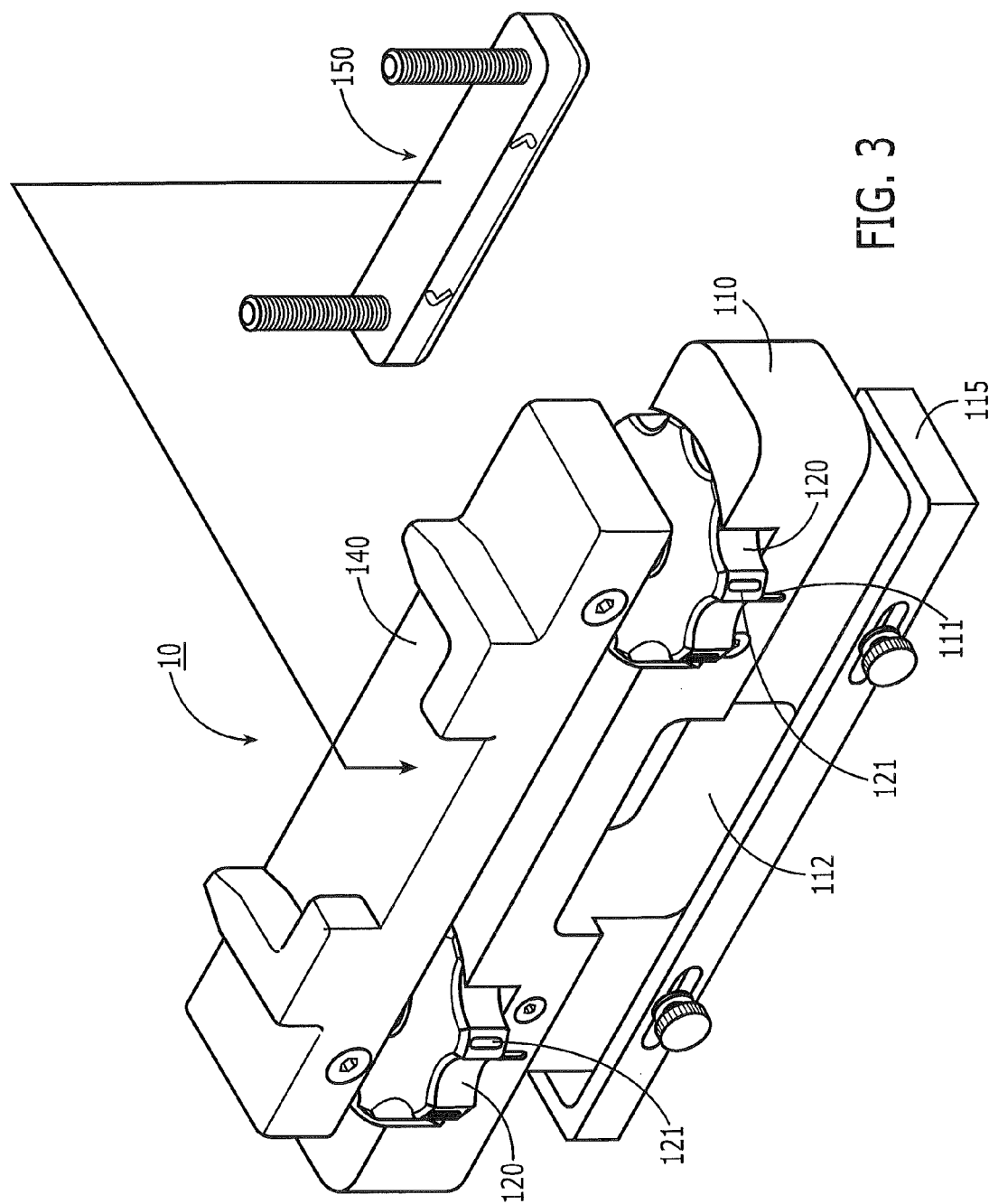
FIG. 3 is an assembled view of the assembly shown in FIG. 2A.

Referring to FIGS. 2A and 3, for example, the stabilizer support 140 can include a top with risers 142 on both sides of an open medial segment 141. A capture block 150 (FIG. 2B, FIG. 7) can reside in the open medial segment 141 with the arrows 151, 152 facing laterally outward from each other.

The capture block 150 can be (typically releasably) directly or indirectly attached to a bottom of the head coil 230 (FIGS. 7 and 8A) via screws 153 or other suitable fixation members. The capture block 150 can be included as an integrated part of the head coil assembly 230 (FIG. 9) or provided as a kit with the table stabilizer 10 or even provided as a separate package for use in the stabilizer assembly as a cooperating component. The capture block 150 can attach directly to the underside of the table extension $T_E$ or to an underside of the head coil assembly 230. The capture block 150 can have different configurations for different head coil and/or table extensions.

A kit with the table stabilizer can include first and second capture blocks of different shapes/sizes and/or configurations to attach to different configurations of the table extensions, e.g., one for the ORT 100 (with round bars) and one for the ORT 200 tables (with square or rectangular bars) in current IMRIS systems. The bars 300 (FIG. 7, 10A-10C) are components of the table head end-extension $T_E$ that slidably attach to the body of the primary table T.

Figure 4:
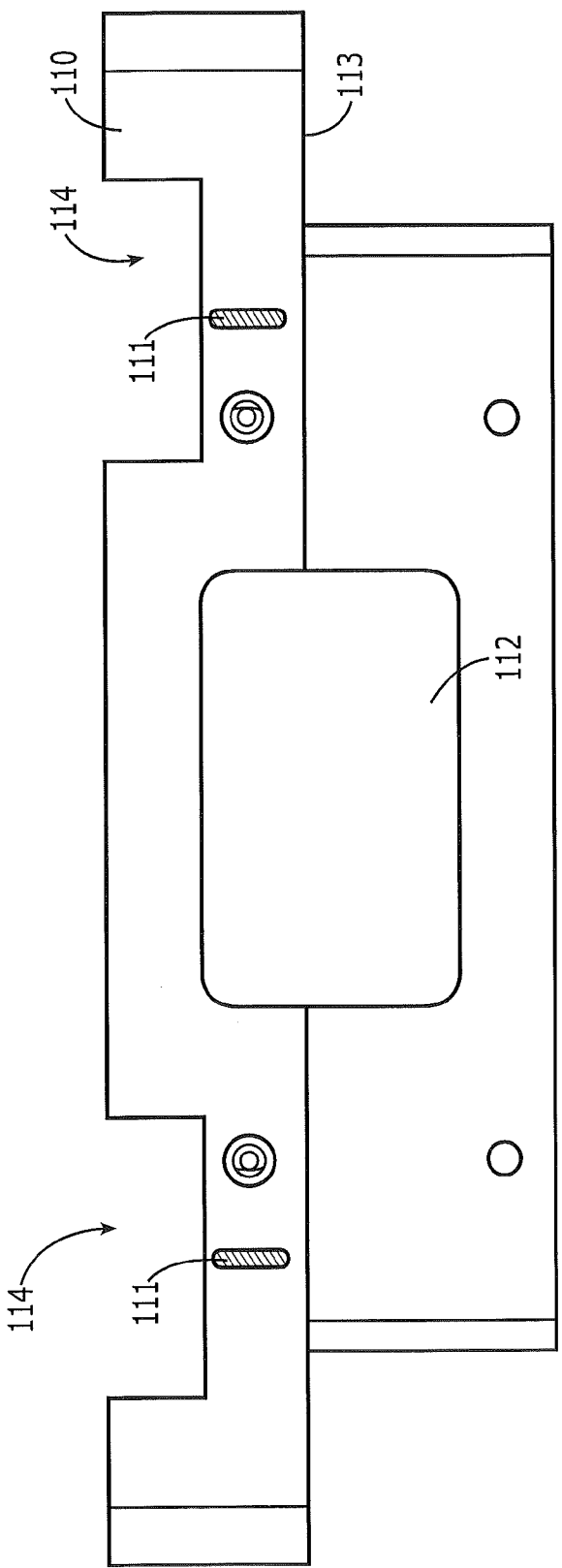
FIG. 4 is a front view of a stabilizer block of the assembly shown in FIG. 2A according to some embodiments of the present invention.

FIGS. 2A and 4 illustrate that the stabilizer block 110 can include holding receptacles 114 that receive a lower end portion 122 of the drive wheels 120.

Figure 10A:
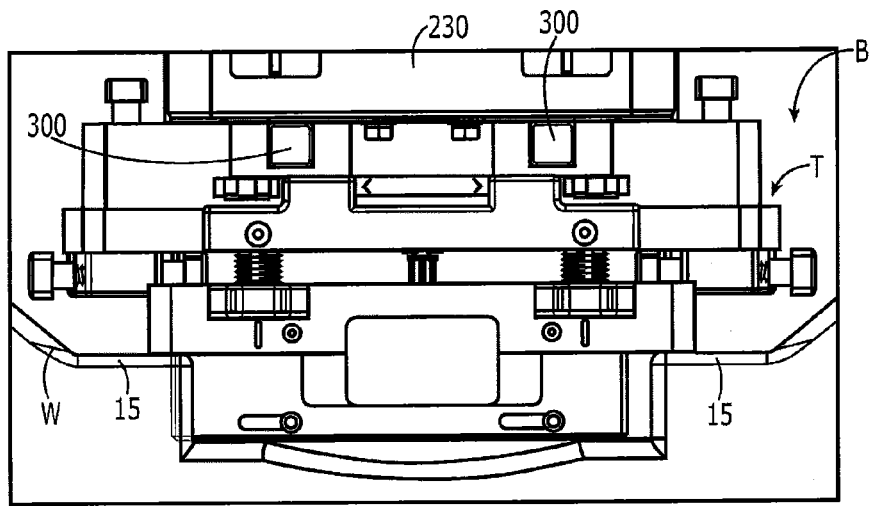
FIGS. 10A-10C are end views of a table stabilizer illustrating lateral adjustability relative to a Scanner bore according to embodiments of the present invention.
Figure 10B:
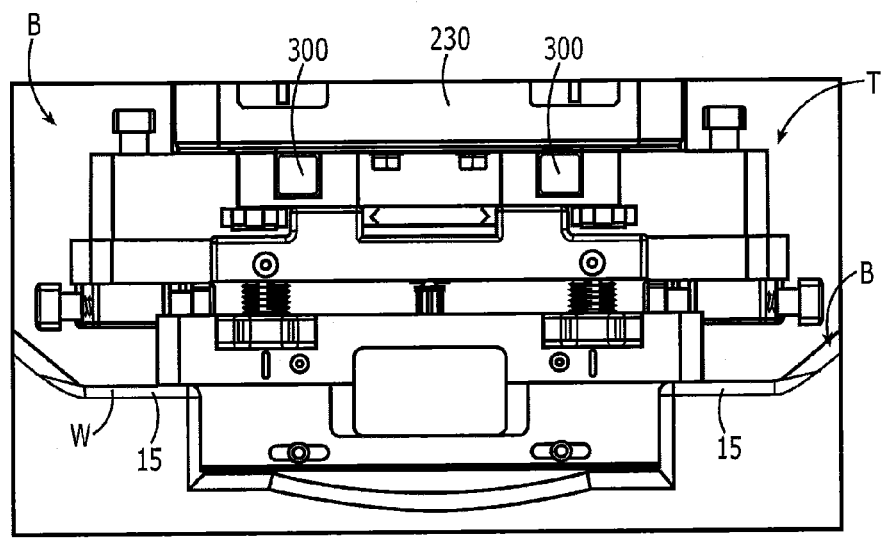
Figure 10C:
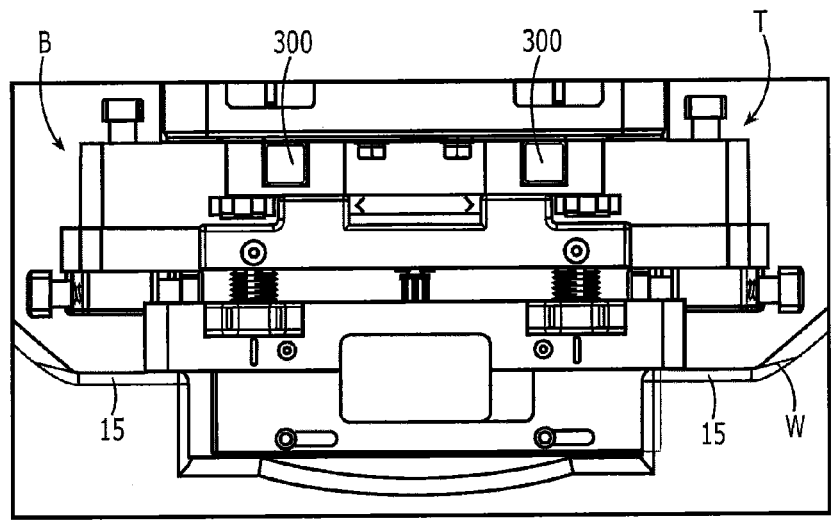

The table stabilizer 10 can also include a lower adjustment slider 115 that can allow the stabilizer block 110 to be laterally adjusted side-to-side via front slots 116 and thumb screws 116s or other attachment members. FIGS. 10A-10C illustrate side to side adjustability with respect to movement in the scanner bore B. In some embodiments, the lateral adjustability can be between about 0.5 inches to about 3 inches, typically about 1 inch.

Figure 6:
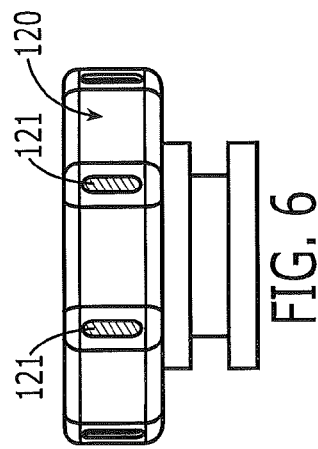
FIG. 6 is a front view of a drive wheel shown in the assembly of FIG. 2A according to embodiments of the present invention.
Figure 8:
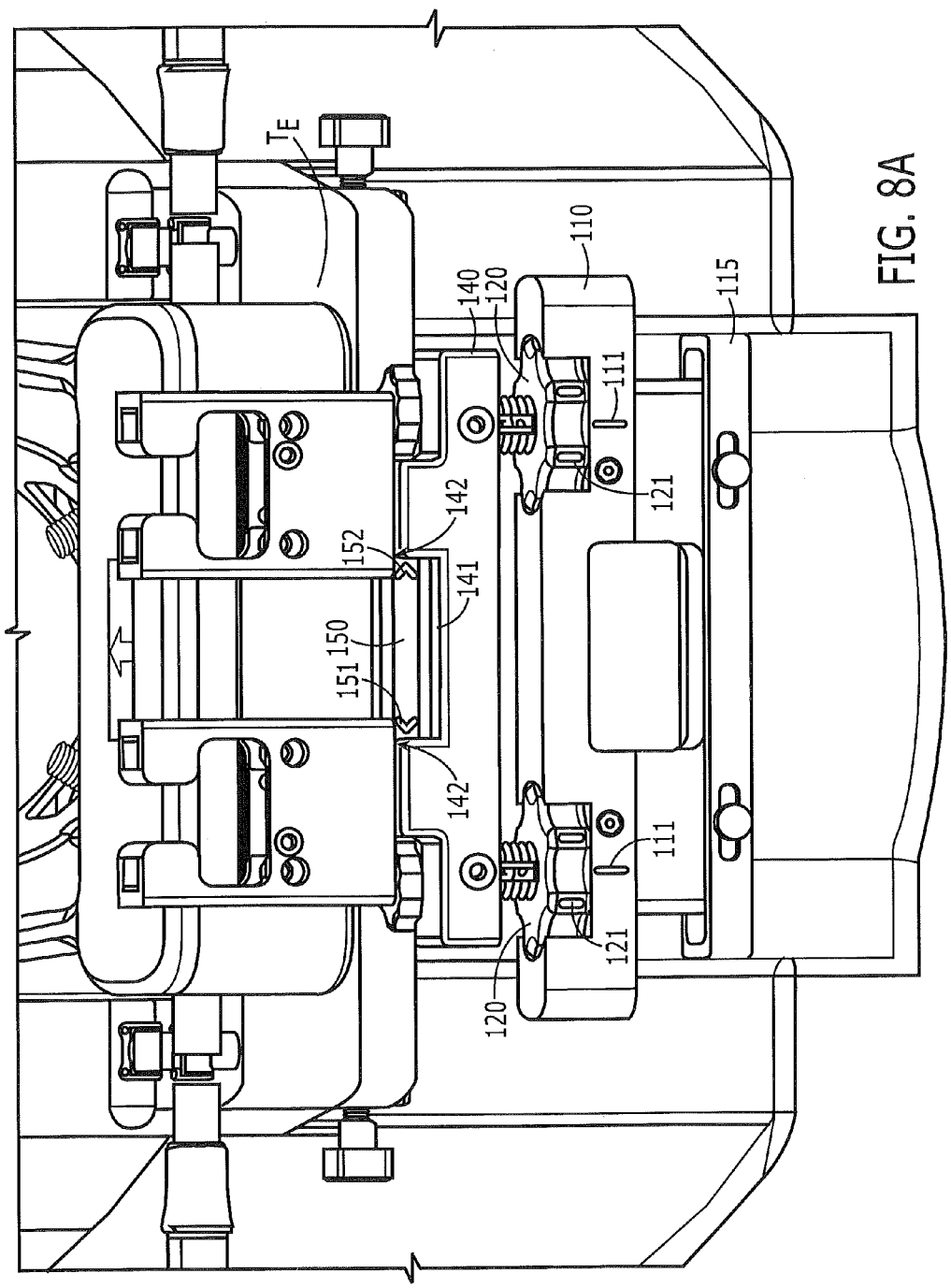
FIG. 8A is a partial front end view of the table stabilizer, head coil and capture block, enlarged relative to the view shown in FIG. 1.
FIG. 8B is an enlarged partial view of the table stabilizer shown in FIG. 8A illustrating different visual indicia for alignment from different components, e.g., different colors according to embodiments of the present invention.

Referring to FIGS. 1A, 3 and 8A, for example, the at least one drive wheel 120 can be a pair of drive wheels and are typically manually rotatable drive wheels. FIGS. 2A and 6 illustrate that the drive wheels 120 can include a grip surface having visual indicia 121 such as elongate marks 121 of a color and/or with visible marking that is different from the adjacent portion of the drive wheel or knob. The stabilizer block 110 can also include visual indicia 111 that may be elongate and that can align with one of the marks 121 as the drive wheel is rotated to lower and raise the stabilizer support 140. The indicia 111, 121 can have the same or different colors 111c, 121c (FIG. 8B) (white is considered a color for purposes of this description), e.g., for different color combinations, one can be darker e.g., black in a lighter perimeter or component, e.g., a white component body, and the other can be darker, e.g., black in a lighter perimeter or component, e.g., black in a white component body, for ease in visualizing the alignment of the cooperating components. Other visual indicia including colors can be used with or without graphic pattern feature.

Figure 5:
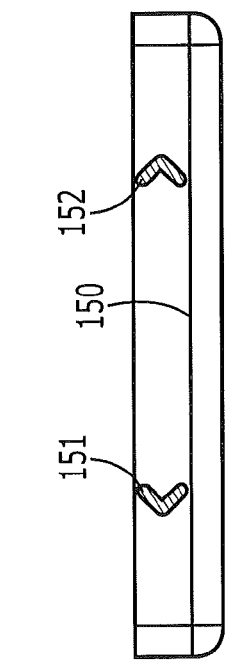
FIG. 5 is a front view of the capture block shown in FIG. 2B.
Figure 7:
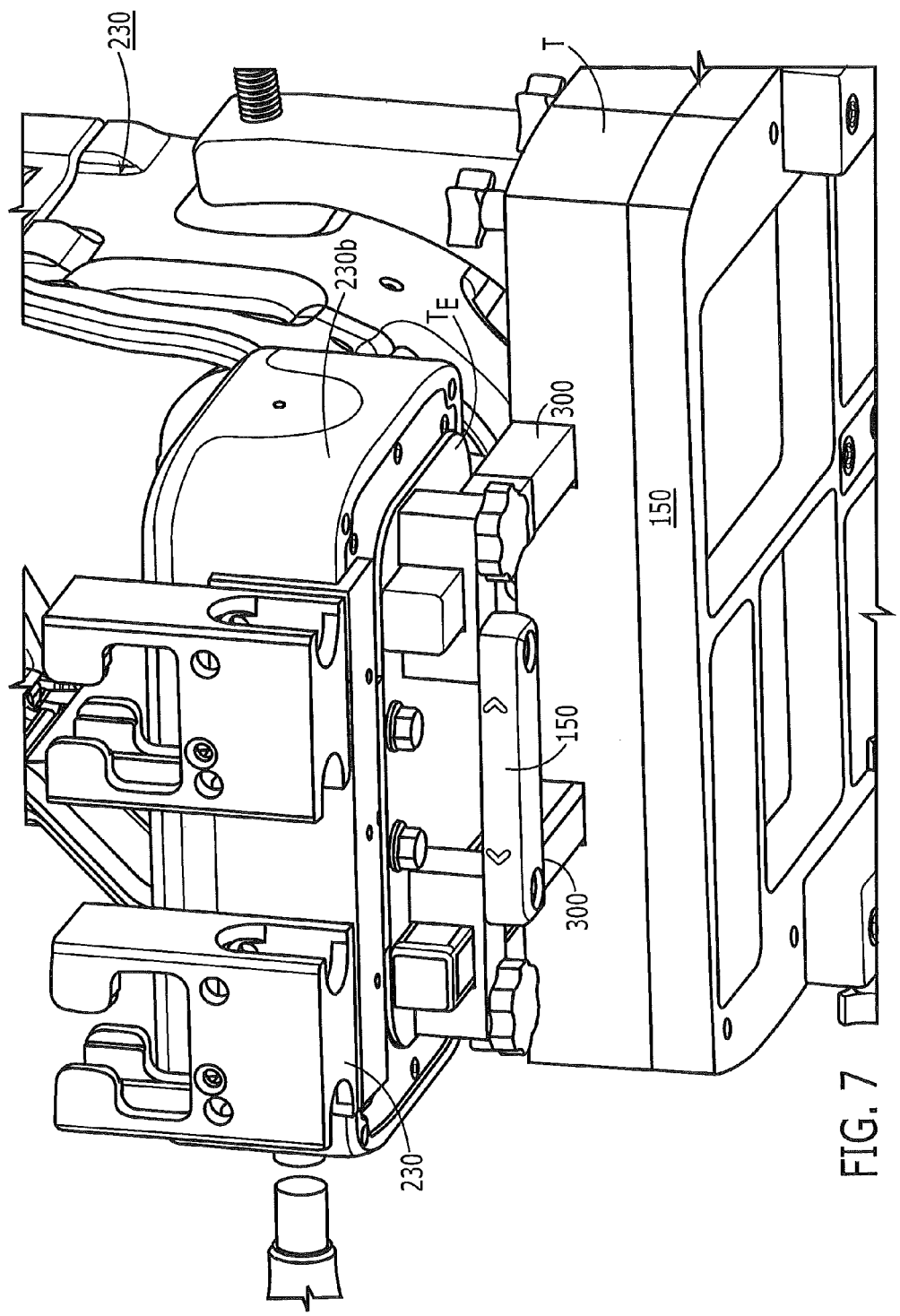
FIG. 7 is a side bottom perspective view of the capture block shown in FIG. 2B attached to a bottom end portion of the head coil according to embodiments of the present invention.

The side-to-side arrows 151, 152 shown in FIGS. 1 and 5 can be of one color that is different from the color of the body of the capture block 150 (e.g., black arrows in a white or lighter colored capture block body).

FIG. 9 illustrates one example of a head coil assembly 230. Details of exemplary head coil assemblies 230 with fixation frames can be found in U.S. patent application Ser. No. 12/685,849, the contents of which are hereby incorporated by reference as if recited in full herein. Near real-time MRI-guided tools and procedures for DBS, as well as for other interventional medical procedures, are being developed. However, the quality of an MRI image depends on the strength of the received signal. As such radio frequency (RF) receiving coils typically are placed in close proximity to the area of a patient being imaged. These coils are often referred to as surface or head coils. One type of head coil used for imaging of the brain is a "bird cage" coil, as described in U.S. Pat. No. 6,396,271. Typically, a birdcage coil has a pair of circular end rings which are bridged by a plurality of equally-spaced straight segments or legs about the periphery of a cylindrical volume. A patient's head fits through one of the end rings and into the enclosed volume and a patient is typically unrestrained and able to move unless used with a head fixation frame assembly as shown. However, other types and configurations of RF coils may also be used as is well known to those of skill in the art.

According to some embodiments of the present invention, the head coil assembly 230 includes a head fixation frame 210 with a base 212, a plurality of upper head fixation members 240, a plurality of lower head fixation members 244, and at least one drive mechanism 342 in communication with the lower head fixation members 244 for advancing and retracting same. The fixation members 240, 244 extend through windows 233 in the upwardly extending arms 231 of the head coil 230c. The head fixation frame 210 includes a pair of upwardly extending spaced-apart arms defining a free space therebetween that holds a portion of the lower arms 231 of the RF head coil 230c. An upper portion of the head coil 242 can have an open space 246 and can releasably attach to the arms 231. The base 212 can attach to a gantry or table via attachment members 204. As noted above, these attachment members 204 may vary depending on the scanner system manufacturer or system itself. The base 212 may have a front end with pockets 248 that that holds MRI compatible cameras.

All of the components of the head fixation assembly 230 and the table stabilizer 10 described above can be formed from or include MRI-compatible material. Exemplary MRI-compatible (non-ferromagnetic) materials include, but are not limited to, various polymeric materials (e.g., plastics), carbon fiber materials, glass-filled epoxies, and metals such as nickel-titanium alloys (e.g., Nitinol) and SST. As known to those skilled in the art of MRI, Nitinol is non-ferromagnetic with a lower magnetic susceptibility than conventional stainless steel.

Figure 11A:
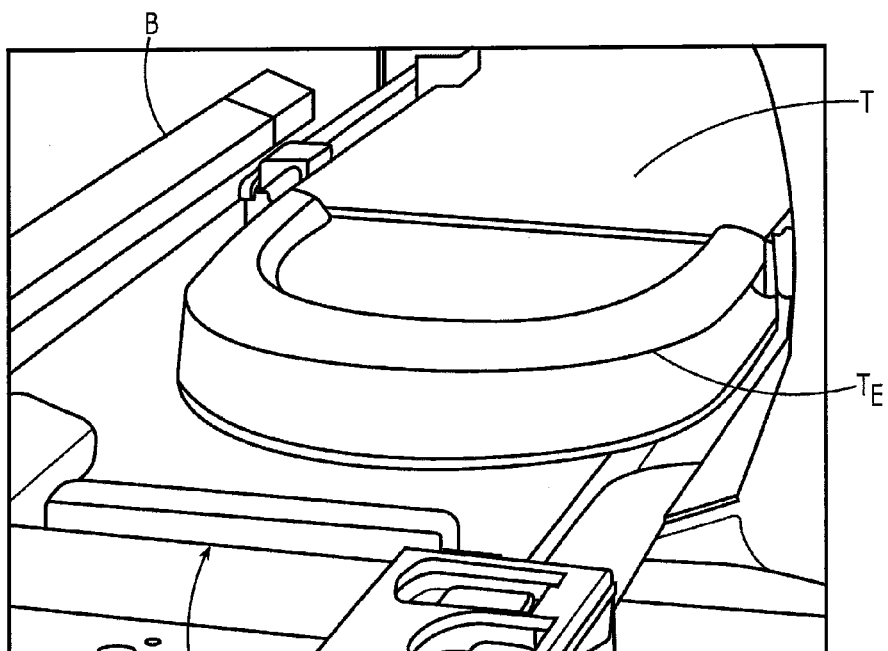
FIGS. 11A-11C illustrate a sequence of table stabilizer configurations that may be used to attach a table stabilizer to a table for use in a scanner bore, according to embodiments of the present invention.
Figure 11B:
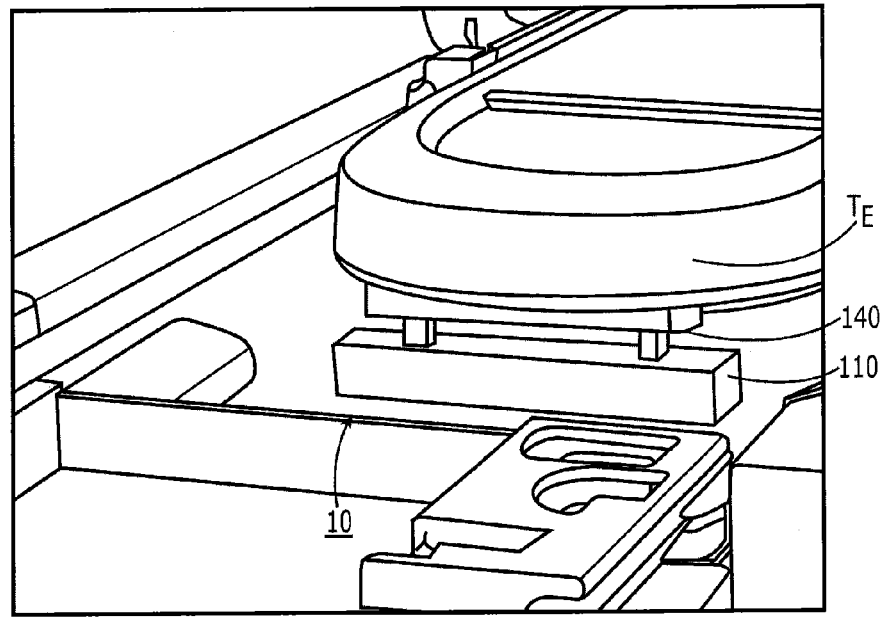
Figure 11C:
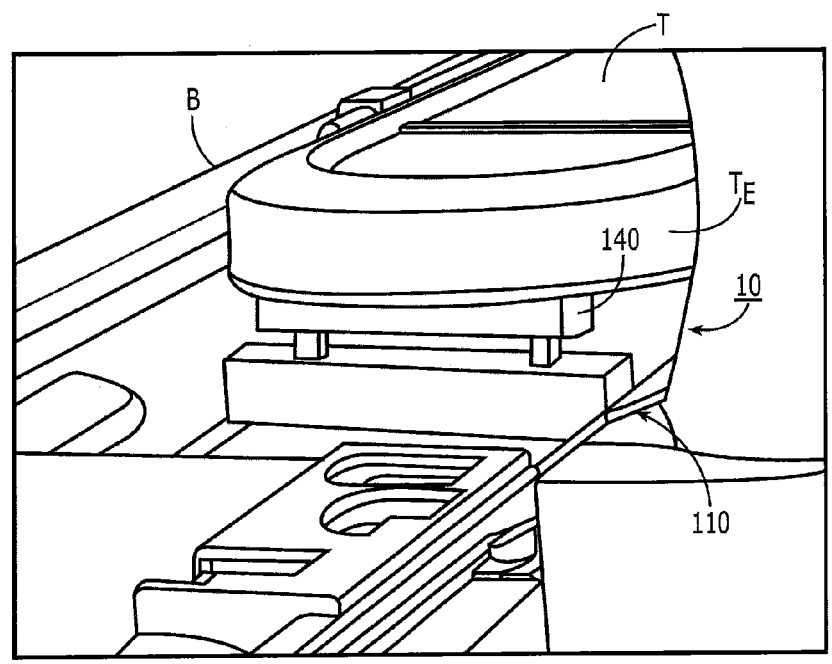

FIGS. 11A-11C illustrate an exemplary sequence of configurations that maybe used to attach the table stabilizer 10 to a table T for use in a scanner bore according to some embodiments of the present invention. The table stabilizer 10 can be aligned with the underside of a front end of the table, then the upper stabilizer support 140 can be raised into snug position. The side to side adjustment for lateral bore alignment (FIGS. 10A-10C) can be carried out after the upper stabilizer is attached to the table T. For stationary scanner systems (with a longitudinally stationary gantry and/or magnet), the table stabilizer 10 can be attached to the table T before the table end $T_E$ is placed in the bore B. For longitudinally moving gantry systems, the table stabilizer 10 can be attached to the table T before or after the table end is in the magnet bore B. Typically, the table stabilizer 10 is attached to the table T in a manner that allows the gantry G to be moved in and out of position with respect to the table T. The arms of the stabilizer block 110 can reside on the support surfaces 15 as the inner lower wall W of the scanner bore B engages the stabilizer block 110. The lateral adjustment can be carried out before a surgical procedure so that the scanner can freely move back and forth as required when a patient is on the table T.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A table stabilizer for a CT and/or MRI Scanner system, comprising:
   a stabilizer block for a table that cooperates with a CT and/or MRI Scanner;
   at least one upwardly extending rod attached to the stabilizer block; and
   an upper stabilizer support attached to the at least one upwardly extending rod to thereby allow the upper stabilizer support to be vertically adjusted relative to the stabilizer block.

2. The table stabilizer of claim 1, further comprising a capture block that is attachable to a head fixation assembly, wherein the upper stabilizer support comprises first and second laterally spaced apart risers residing on opposing sides of an open medial segment, and wherein the capture block is configured to be received in the open medial segment to rest on the upper stabilizer support.

3. The table stabilizer of claim 1, wherein the stabilizer block comprises at least one drive wheel attached to a respective at least one upwardly extending rod to allow a user to turn the drive wheel to vertically adjust the height of the upper stabilizer support relative to the stabilizer block.

4. The table stabilizer of claim 3, wherein the at least one upwardly extending rod comprises first and second laterally spaced apart upwardly extending threaded rods, and wherein the at least one stabilizer block comprises first and second laterally spaced apart drive wheels, the first drive wheel attached to the first upwardly extending threaded rod and the second drive wheel attached to the second upwardly extending threaded rod.

5. The table stabilizer of claim 1, wherein the stabilizer block comprises a lower lateral adjustment slider configured as a base with laterally extending slots that holds the stabilizer block and allows a user to laterally adjust the position of the stabilizer block in the base.

6. The table stabilizer of claim 1, wherein the at least one upwardly extending rod comprises visual indicia of height and/or position.

7. The table stabilizer of claim 4, wherein the threaded rods each comprise a scale for visual indicia of height and/or position, wherein the first and second drive wheels comprise circumferentially spaced apart visual indicia for identifying a rotational position, wherein the stabilizer block comprises first and second receptacles in an upper surface of the stabilizer block, the first receptacle holding the first drive member and the second receptacle holding the second drive member, each receptacle configured so that an outer perimeter of a respective drive wheel extends outside a corresponding receptacle to allow a user to rotate the drive wheel while held in the corresponding receptacle, and wherein the stabilizer block includes visual indicia of alignment, positioned adjacently below each of the first and second receptacles.

8. The table stabilizer of claim 3, wherein the stabilizer block comprises a pair of outwardly extending upper arms on opposing lateral sides thereof that slidably rest on support surfaces of a bore of the CT and/or MRI gantry, and wherein the stabilizer block comprises at least one receptacle in an upper surface of the stabilizer block that holds a respective one of the at least one drive member.

9. The table stabilizer of claim 2, wherein the capture block comprises laterally extending arrows to thereby provide visual alignment indicia for placement in the medial open segment between the risers.

10. The table stabilizer of claim 1, wherein all components are fabricated from MRI compatible material.

11. An MRI or CT Scanner system, comprising:
a CT or MRI Scanner having a gantry and a bore extending through the gantry;
a patient table configured to be received in the bore of the gantry; and
a table stabilizer that resides under and is attached to one end portion of the table and that is supported by a floor also supporting the patient table.

12. The system of claim 11, wherein the table stabilizer comprises:
a stabilizer block configured to engage support surfaces of an inner wall of the bore of the gantry;
at least one upwardly extending rod attached to the stabilizer block; and
an upper stabilizer support attached to the at least one upwardly extending rod to thereby allow the upper stabilizer support to be vertically adjusted relative to the stabilizer block.

13. The system of claim 11, wherein the table stabilizer further comprises a capture block that is attachable to a head fixation assembly and/or a table extension, wherein the upper stabilizer support comprises first and second laterally spaced apart risers residing on opposing sides of an open medial segment, and wherein the capture block is configured to be snugly received in the open medial segment to rest on the upper stabilizer support.

14. The system of claim 12, wherein the stabilizer block comprises at least one drive wheel attached to a respective at least one upwardly extending rod to allow a user to turn the drive wheel to vertically adjust the height of the upper stabilizer support relative to the stabilizer block.

15. The system of claim 14, wherein the at least one upwardly extending rod comprises first and second laterally spaced apart upwardly extending threaded rods, and wherein the at least one drive wheel comprises first and second laterally spaced apart drive wheels, the first drive wheel attached to the first upwardly extending threaded rod and the second drive wheel attached to the second upwardly extending threaded rod.

16. The system of claim 12, wherein the stabilizer block comprises a lower lateral adjustment slider configured as a base with laterally extending slots that holds the stabilizer block and allows a user to laterally adjust the position of the stabilizer block in the base.

17. The system of claim 12, wherein the at least one upwardly extending rod comprises visual indicia of height or position.

18. The system of claim 15, wherein the threaded rods each comprise a scale for visual indicia of height and/or position, wherein the drive wheels comprise circumferentially spaced apart visual indicia for identifying a rotational position, wherein the stabilizer block comprises first and second receptacles in an upper surface of the stabilizer block, the first receptacle holding the first drive member and the second receptacle holding the second drive member, each receptacle configured so that an outer perimeter of a respective drive wheel extends outside a corresponding receptacle to allow a user to rotate the drive wheel while held in the corresponding receptacle, and wherein the stabilizer block includes visual indicia of alignment, positioned adjacently below each of the first and second receptacles.

19. The system of claim 14, wherein the stabilizer block comprises a pair of outwardly extending upper arms on opposing lateral sides thereof that slidably rest on support surfaces of an inner wall of the gantry bore, and wherein the stabilizer block comprises at least one receptacle in an upper surface of the stabilizer block that holds a respective one of the at least one drive member.

20. The system of claim 13, wherein the capture block comprises laterally extending arrows to thereby provide visual alignment indicia for placement in the medial open segment between the risers.

21. The system of claim 11, wherein the system is an MRI system with a movable magnet having the gantry with the bore, wherein the patient table comprises a pedestal that is stationary and affixed to a floor, wherein the table stabilizer engages an inner wall of the bore of the magnet, and wherein all the table stabilizer components are fabricated from MRI compatible material.

22. An MRI Scanner, comprising:
a longitudinally moving gantry with a magnet having a bore with an inner wall;
a patient table supported by a pedestal to be in a fixed position on a floor;
a table stabilizer residing under and attached to (i) a table extension and/or an MRI compatible head support frame and (ii) a lower portion of the inner wall of the gantry bore, and wherein the table stabilizer is configured to have lateral and vertical adjustability relative to the patient table and/or position in the magnet bore.

23. A method of supporting a head coil in a bore of a magnet of an MRI Scanner during an MRI-guided procedure, comprising:
providing a head fixation assembly with a head coil;
providing a patient table with a table stabilizer attached thereto so as to reside under a table extension and/or head end portion of the patient table;

placing a patient on the patient table with a head of the patient in the head fixation assembly;

moving either (a) the patient table with the table stabilizer or (b) moving the magnet so that the patient on the patient table resides in the magnet bore and the table stabilizer engages an inner wall of the bore of the magnet; and performing an MRI-guided procedure with the patient on the patient table in the magnet bore thereby providing additional structural rigidity/support to inhibit downward movement of the head fixation assembly due to pressure applied to the head of a patient held in the head fixation assembly during an MRI guided procedure.

24. The method of claim 23, wherein the moving step is carried out by moving the magnet while the patient table is in a fixed position using a pedestal support.

* * * * *